United States Patent [19]

Harandi et al.

[11] Patent Number: 5,064,623
[45] Date of Patent: Nov. 12, 1991

[54] INTEGRATED SYSTEM FOR EXTRACTION OF CRUDE ALCOHOL AND CO-CONVERSION RAFFINATE WITH OLEFIN

[75] Inventors: Mohsen N. Harandi, Lawrenceville; Hartley Owen, Belle Mead, both of N.J.

[73] Assignee: Mobil Oil Corporation, Fairfax, Va.

[21] Appl. No.: 308,237

[22] Filed: Feb. 9, 1989

Related U.S. Application Data

[63] Continuation-in-part of Ser. No. 179,726, Apr. 11, 1988, Pat. No. 4,827,056.

[51] Int. Cl.$^5$ .............................................. B01J 8/04
[52] U.S. Cl. .................................... 422/190; 202/152; 203/DIG.6; 422/187; 422/189; 422/256
[58] Field of Search ............... 422/187, 189, 190, 256; 202/152; 203/DIG. 6

[56] References Cited

U.S. PATENT DOCUMENTS 4,560,537 12/1985 Tabak ................................ 422/190

Primary Examiner—Jill Johnston
Attorney, Agent, or Firm—Alexander J. McKillop; Charles J. Speciale; L. G. Wise

[57] ABSTRACT

An improved reactor system reacts crude aqueous methanol feedstock with iso-olefinic hydrocarbons to produce $C_5^+$ methyl t-alkyl ethers. The system includes an extractor for contacting the aqueous methanol feedstock with a liquid hydrocarbon extraction solvent rich in $C_4^+$ isoalkene. Both an organic extract phase and an aqueous methanol raffinate phase recovered from the extractor and fed to a primary reactor. This primary reactors reacts the methanol and $C_4^+$ isoalkene from the organic extract phase under catalytic conditions to produce an ether product. The ether product is fed to an etherification effluent fractionator to separate the ether product from unreacted methanol and $C_4^+$ isoalkene. A secondary reactor then converts methanol from the aqueous methanol raffinate phase with the unreacted methanol and $C_4^+$ isolakene to produce hydrocarbons.

6 Claims, 2 Drawing Sheets 5,064,623

INTEGRATED SYSTEM FOR EXTRACTION OF CRUDE ALCOHOL AND CO-CONVERSION RAFFINATE WITH OLEFIN

REFERENCE TO COPENDING APPLICATION

This application is a continuation-in-part of U.S. patent application Ser. No. 179,726, filed Apr. 11, 1988, now U.S. Pat. No. 4,827,046, incorporated herein by reference.

BACKGROUND OF THE INVENTION

This invention relates to integrated reactor and extraction systems and operating techniques for converting crude methanol or the like to lower methyl tertiary-alkyl ethers, such as MTBE. In particular, this invention relates to a system for converting crude methanol to valuable products by etherifying lower branched olefins, such as $C_4$-$C_7$ normally liquid iso-olefins.

It is known that isobutylene and other isoalkenes produced by hydrocarbon cracking may be reacted with methanol over an acidic catalyst to provide methyl tertiary butyl ether (MTBE) and isoamylenes may be reacted with methanol over an acidic catalyst to produce tertiary-amyl methyl ether (TAME). Those ethers having the formula $CH_3$—O—R, where R is a tertiary alkyl radical, are particularly useful as octane improvers for liquid fuels, especially gasoline.

MTBE and TAME are known to be high octane ethers. The article by J. D. Chase, et al., *Oil and Gas Journal*, Apr. 9, 1979, discusses the advantages one can achieve by using these materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114.

Increasing demand for high octane gasolines blended with lower aliphatic alkyl ethers as octane boosters and supplementary fuels has created a significant demand for isoalkylethers, especially the $C_5$ to $C_7$ methyl alkyl ethers, such as methyl tertiary butyl ether (MTBE) and tertiary amyl methyl ether (TAME). Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt %; however, the present invention is useful for removing water in lesser amounts or greater.

It is main object of the present invention to provide a novel and economic technique for removing excess water from crude methanol feedstocks, including novel reactor systems and equipment for treating oxygenate feedstocks prior to etherification and disposing of raffinate containing methanol. It has been discovered that aqueous methanol streams, such as etherification feedstock extraction byproduct can be economically upgraded by catalytic conversion concurrently with hydrocarbons.

SUMMARY OF THE INVENTION

A continuous technique has been found for converting crude alcohol to lower alkyl t-alkyl ethers. In a preferred embodiment, a continuous feedstock separation and etherification reactor system is provided for converting crude methanol feedstock to methyl t-alkyl ether. This system includes: extractor means for contacting crude feedstock liquid containing a minor amount of water with a liquid olefinic hydrocarbon extraction stream under extraction conditions favorable to selective extraction of methanol, thereby providing an extract liquid stream rich in methanol and an aqueous raffinate stream lean in methanol; first catalytic reactor means operatively connected for contacting the extract stream in a catalytic reaction zone with acid etherification catalyst in an etherification reaction zone under process conditions to convert a major portion of methanol to ether; effluent separation means for recovering ether product from unconverted olefinic hydrocarbon and methanol; and second catalytic reactor means operatively connected for contacting said raffinate stream with conversion catalyst in the presence of said unconverted olefinic hydrocarbon and methanol to produce normally liquid hydrocarbon product.

These and other objects and features of the invention will be understood from the following description and in the drawing.

DRAWING

FIG. 1 of the drawing is a schematic etherification system flowsheet depicting the present invention; and FIG. 2 is a typical fluidized bed reactor system useful for upgrading hydrocarbons and co-converting raffinate.

DETAILED DESCRIPTION

Figure 1:
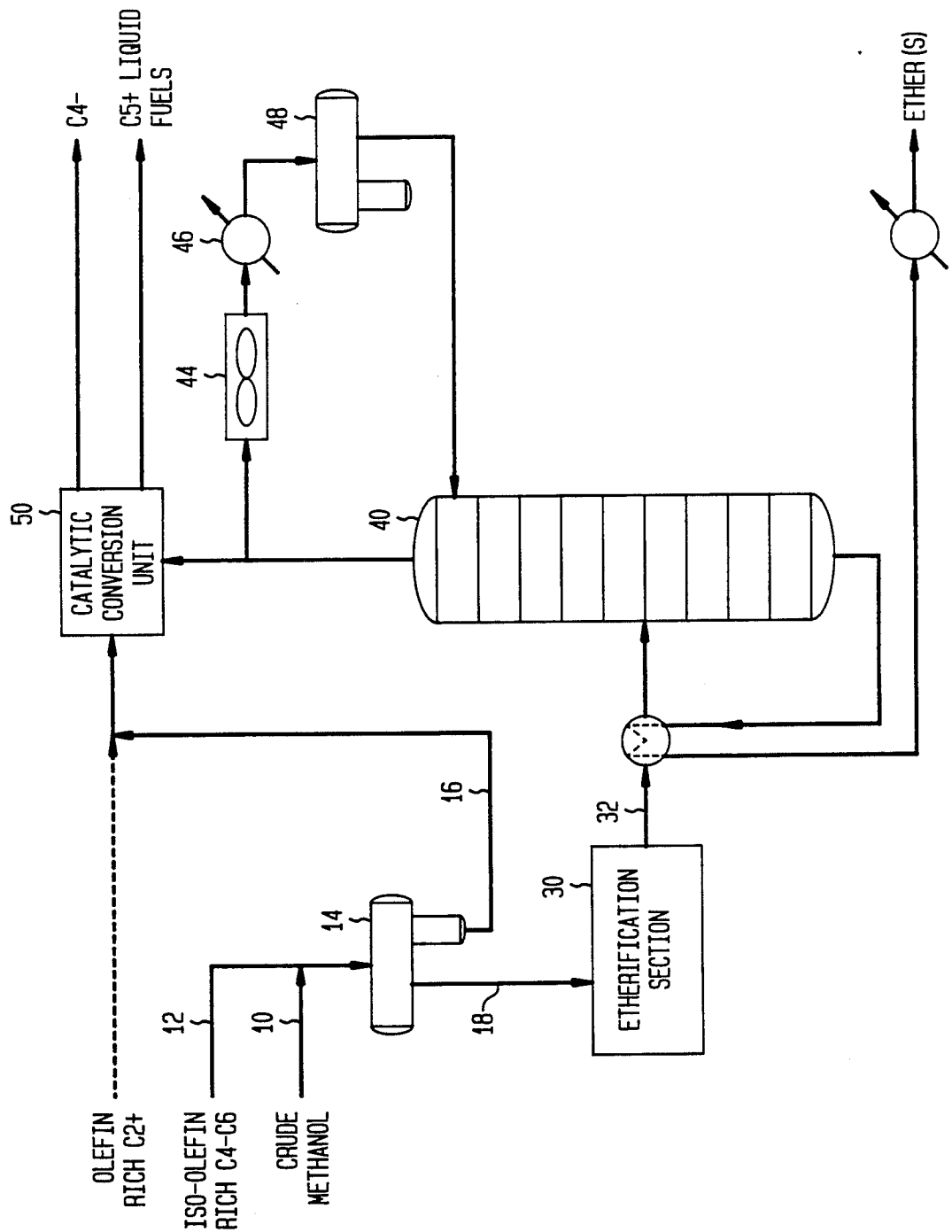

Typical feedstock materials for etherification reactions include olefinic streams, such as FCC light naphtha and butenes rich in isoolefins. These aliphatic streams are produced in petroleum refineries by catalytic cracking of gas oil or the like. The crude methanol commercially available from syngas processes may contain, for instance 4 to 17 wt % water, which must be removed, preferrably to a methanol purity of about 99.8 wt %. It has been found that more than 75% of crude feedstock methanol can be recovered by liquid extraction with light olefinic liquid extractant, such as butenes and $C_5$+ light olefinic naphtha. The typical feed ratio range is about 5 to 20 parts hydrocarbon extractant per part by volume of methanol.

Typical equipment according to the present invention includes a continuous feedstock separation and etherification reactor system for converting crude methanol oxygenate feedstock and isoolefin to methyl t-alkyl ether, wherein the unit operation apparatus includes: extractor means for contacting crude feedstock liquid containing a minor amount of water with a liquid hydrocarbon extraction stream under extraction conditions favorable to selective extraction of methanol, thereby providing an extract liquid stream rich in methanol and an aqueous raffinate stream lean in methanol; first catalytic reactor means operatively connected for contacting the extract stream in a catalytic reaction zone with acid etherification catalyst in an etherification reaction zone under process conditions to convert a major portion of methanol to ether; second catalytic reactor means for contacting said raffinate stream with methanol conversion catalyst in the presence of hydrocarbon to produce a liquid hydrocarbon stream; and means for charging at least a portion of said liquid hydrocarbon stream from said second reactor means to said extractor means as said extraction stream.

Referring to the drawing, a continuous stream of crude methanol (MeOH) feedstock is introduced via conduit 10 with a stream of $C_4+$ olefinic hydrocarbon liquid extractant introduced via conduit 12 to a top inlet of extraction separation unit 14, operated at about 35°–40° C. These streams are contacted under liquid extraction conditions to provide an aqueous raffinate phase. An aqueous stream containing a major amount of the water present in the crude feedstock is withdrawn via conduit 16. The lighter organic extract phase containing hydrocarbon extraction solvent and the major amount of feedstock methanol is recovered from extraction unit 14 via conduit 18, and introduced under temperature and process conditions suitable for conversion of methanol in contact with etherification catalyst in reactor system 30. From reactor 30, the effluent product stream passes via line 32 to a debutanizer or, optionally, depentanizer fractionation tower 40.

In separation unit 40 the $C_5+$ methyl tert-alkyl ether product is recovered as a liquid product, along with unreacted C5-C6 hydrocarbons in the extractant. Tower overhead comprising unreacted $C_4+$ hydrocarbons and methanol are passed via condenser means 44, 46 to liquid accumulator 48. The debutanizer overhead vapor stream is sent to catalytic conversion unit 50, where it is contacted concurrently with aqueous raffinate from line 16, and optionally lower olefins rich in C2-C5 light hydrocarbons.

The aqueous raffinate stream 16 consists essentially of water, partitioned methanol (50–80 wt %) and a trace of hydrocarbon. This stream is reactive at elevated temperature in the presence of an acid zeolite catalyst, such as medium pore shape selective zeolite, such as , ZSM-5, etc., in a fluidized bed reaction zone. For example, the aqueous methanol raffinate stream may be coreacted with olefinic light gas and/or other reactive hydrocarbon feedstreams in an oligomerization reaction section, as described by Owen et al in U.S. Pat. No. 4,788,365, incorporated herein by reference. The aqueous methanol may be introduced as a liquid directly to the reaction zone (bottom or middle section), as herein described with regard to FIG. 2, or vaporized and mixed with hydrocarbon feed. Optionally, FCC fuel gas containing ethene may be injected at the bottom of the fluidized bed reaction zone and converted along with the raffinate stream as herein described.

EXTRACTION UNIT OPERATION

The typical preferred crude feedstock material is methanol containing about 4 to 17% by weight water. The extraction contact unit may be a stirred multi-stage vertical extraction column adapted for continuous operation at elevated pressure. Any suitable extraction equipment may be employed, including cocurrent, cross-current or single contactors, wherein the liquid methanol feedstock is intimately contacted with a substantially immiscible liquid hydrocarbon solvent, which may be a mixture of $C_4+$ aliphatic components including lower alkanes, n-alkenes or relatively pure isoalkenes, such as isobutylene, etc. This unit operation is described in Kirk-Othmer Encyclopedia of Chemical Technology (Third Ed.), 1980, pp. 672-721. Other equipment for extraction is disclosed in U.S. Pat. Nos. 4,349,415 (DeFilipi et al), 4,626,415 (Tabak), and 4,665,237 (Arakawa et al). Unit operation details are also disclosed by Harandi et al in copending U.S. patent application Ser. No. 043729, filed Apr. 29, 1987, now U.S. Pat. No. 4,831,195 incorporated herein by reference. The methanol extraction step can be performed advantageously in a countercurrent multistage design, such as a simple packed column, rotating disk column, agitated column with baffles or mesh, or a series of single stage mixers and settlers.

As an example of typical methanol extraction with FCC light naphtha in a liquid-liquid contact and separation unit for extracting crude methanol containing 4 wt % water at about 38° C. (100° F.). The extractor unit and water wash unit are operated at about 35°–65° C. (100°–150° F.) and 0–2000 kPa. The stream composition for each feed, light extract phase and heavy raffinate phase is given in Table I.

TABLE 1

| | Extraction Operation | | | |
|---|---|---|---|---|
| Component | FCC Light Naphtha | Crude Methanol | Light Liquid Phase | Raffinate Heavy Liquid Phase |
| Methanol (lbmol/hr) | 149.87 | 113.96 | 35.91 | |
| Water | | 11.11 | 0.40 | 10.71 |
| $C_4$ | 51.13 | | 50.98 | 0.15 |
| $C_5$ | 330.10 | | 329.23 | 0.87 |
| $C_6$ | 163.38 | | 163.02 | 0.36 |
| Total | 544.61 | 160.98 | 657.59 | 48.00 |
| Methanol Recovered (wt %) | | | 76.0 | |
| Water Entrained in Methanol | | | 0.2* | |

(*based on dry hydrocarbon feed)

Etherification Operation

The reaction of methanol with isobutylene and isoamylenes at moderate conditions with a resin catalyst is known technology, as provided by R. W. Reynolds, et al., *The Oil and Gas Journal*, June 16, 1975, and S. Pecci and T. Floris, *Hydrocarbon Processing*, December 1977. An article entitled "MTBE and TAME—A Good Octane Boosting Combo", by J. D. Chase, et al., *The Oil and Gas Journal*, Apr. 9, 1979, pages 149-152, discusses the technology. A preferred catalyst is a polyfunctional ion exchange resin which etherifies and isomerizes the reactants. A typical acid catalyst is Amberlyst 15 sulfonic acid resin.

Processes for producing and recovering MTBE and other methyl tert-alkyl ethers for $C_4$-$C_7$ isoolefins are known to those skilled in the art, such as disclosed in U.S. Pat. Nos. 4,544,776 (Osterburg et al) and 4,603,225 (Colaianne et al). Various suitable extraction and distillation techniques are known for recovering ether and hydrocarbon streams from etherication effluent.

CONVERSION OF METHANOL AND HYDROCARBONS TO LIQUID HYDROCARBONS

Zeolite catalysis technology for upgrading lower aliphatic hydrocarbons and oxygenates to liquid hydrocarbon products are well known. Commerial Methanol-to-Gasoline (MTG), methanol-to olefins (MTO), aromatization (M2-Forming) and Mobil Olefin to Gasoline/Distillate (MOG/D) processes employ shape selective medium pore zeolite catalysts for these processes. It is understood that the present zeolite conversion unit operation can have the characteristics of these catalysts and processes to produce a variety of hydrocarbon products, especially liquid aliphatic and aromatics in the C5-C9 gasoline range.

Description of Zeolite Catalysts

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, Fe or mixtures thereof, within the zeolitic framework. These medium pore zeolites are favored for acid catalysis; however, the advantages of ZSM-5 structures may be utilized by employing highly siliceous materials or cystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

Zeolite hydrocarbon upgrading catalysts preferred for use herein include the medium pore (i.e., about 5-7A) shape-selective crystalline aluminosilicate zeolites having a silica-to-alumina ratio of at least 12, a constraint index of about 1 to 12 and acid cracking activity (alpha value) of about 1-250, preferably about 3 to 80 based on total catalyst weight. In the fluidized bed reactor the coked catalyst may have an apparent activity (alpha value) of about 10 to 80 under the process conditions to achieve the required degree of reaction severity. Representative of the ZSM-5 type medium pore shape selective zeolites are ZSM-5, ZSM-11, ZSM-12, ZSM-22, ZSM-23, ZSM-35, and ZSM-48. Aluminosilicate ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245; 4,414,423; 4,417,086; 4,517,396 and 4,542,251. The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified if desired to adjust acidity and oligomerization/aromatization characteristics. A typical zeolite catalyst component having Bronsted acid sites may consist essentially of aluminosilicate ZSM-5 zeolite with 5 to 95 wt. % silica and/or alumina binder.

These siliceous zeolites may be employed in their acid forms, ion exchanged or impregnated with one or more suitable metals, such as Ga, Pd, Zn, Ni, Co and/or other metals of Periodic Groups III to VIII. The zeolite may include a hydrogenation-dehydrogenation component (sometimes referred to as a hydrogenation component) which is generally one or more metals of group IB, IIB, IIIB, VA, VIA or VIIIA of the Periodic Table (IUPAC), especially aromatization metals, such as Ga, Pd, etc. Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (eg, ionic $Ni^{+2}$, and a shape-selective medium pore acidic oligomerization catalyst, such as ZSM-5 zeolite) which components may be present in admixture or combined in a unitary bifunctional solid particle. It is possible to utilize an ethene dimerization metal or oligomerization agent to effectively convert feedstock ethene in a continuous reaction zone.

Certain of the ZSM-5 type medium pore shape selective catalysts are sometimes known as pentasils. In addition to the preferred aluminosilicates, the gallosilicate, and ferrosilicate materials may be employed. ZSM-5 type pentasil zeolites are particularly useful in the process because of their regenerability, long life and stability under the extreme conditions of operation. Usually the zeolite crystals have a crystal size from about 0.01 to 2 microns or more. In order to obtain the desired particle size for fluidization in the turbulent regime, the zeolite catalyst crystals are bound with a suitable inorganic oxide, such as silica, alumina, etc. to provide a zeolite concentration of about 5 to 95 wt. %. It is advantageous to employ a standard ZSM-5 having a silica:alumina molar ratio of 25:1 or greater in a once-through fluidized bed unit to convert 60 to 100 percent, preferably at least 75 wt %, of the monoalkenes and methanol in a single pass. In the preferred embodiment 25% H-ZSM-5 catalyst calcined with 75% silica-alumina matrix binder is employed unless otherwise stated.

Particle size distribution can be a significant factor in achieving overall homogeneity in turbulent regime fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 32 microns. Accordingly, the fluidization regime is controlled to assure operation between the transition velocity and transport velocity.

Fluidized Bed Reactor Operation

Suitable olefinic feedstreams to the olefin upgrading unit comprise $C_2-C_5$ alkenes, including unreacted butylenes and amylenes from the etherification operation. Non-deleterious components, such as $C_1-C_2$ lower paraffins and inert gases, may be present. The reaction severity conditions can be controlled to optimize yield of olefinic gasoline or $C_6-C_8$ BTX hydrocarbons, according to product demand. It is understood that aromatic hydrocarbon and light paraffin production is promoted by those zeolite catalysts having a high concentration of Bronsted acid reaction sites. Accordingly, an important criterion is selecting and maintaining catalyst inventory to provide either fresh or regenerated catalyst having the desired properties. Reaction temperatures and contact time are also significant factors in the reaction severity, and the process parameters are followed to give a substantially steady state condition wherein the reaction severity is maintained within the limits which yield a desired weight ratio of propane to propene in the reaction effluent.

In a turbulent fluidized catalyst bed the conversion reactions are conducted in a vertical reactor column by passing hot reactant vapor or lift gas upwardly through the reaction zone at a velocity greater than dense bed transition velocity and less than transport velocity for the average catalyst particle. A continuous process is operated by withdrawing a portion of coked catalyst from the reaction zone, oxidatively regenerating the withdrawn catalyst and returning regenerated catalyst to the reaction zone at a rate to control catalyst activity and reaction severity to effect feedstock conversion.

Upgrading of olefins by such hydrogen contributors in co-conversion reactors is taught by Owen et al in U.S. Pat. No. 4,788,365 and 4,090,949. In a typical process, the methanol and olefinic feedstream is converted in a catalytic reactor under oligomerization conditions and moderate pressure (ie-100 to 2500 kPa) to produce a predominantly liquid product consisting essentially of $C_5+$ hydrocarbons rich in gasoline-range mono-olefins and aromatics. The use of fluidized bed catalysis permits the conversion system to be operated at low pressure drop, which in an economically practical operation can provide a maximum operating pressure only 50 to 200 kPa above atmospheric pressure. Another important advantage is the close temperature control that is made possible by turbulent regime operation, wherein the uniformity of conversion temperature can be maintained within close tolerances, often less than 5° C. Except for a small zone adjacent the bottom gas inlet, the midpoint measurement is representative of the entire bed, due to the thorough mixing achieved.

Figure 2:
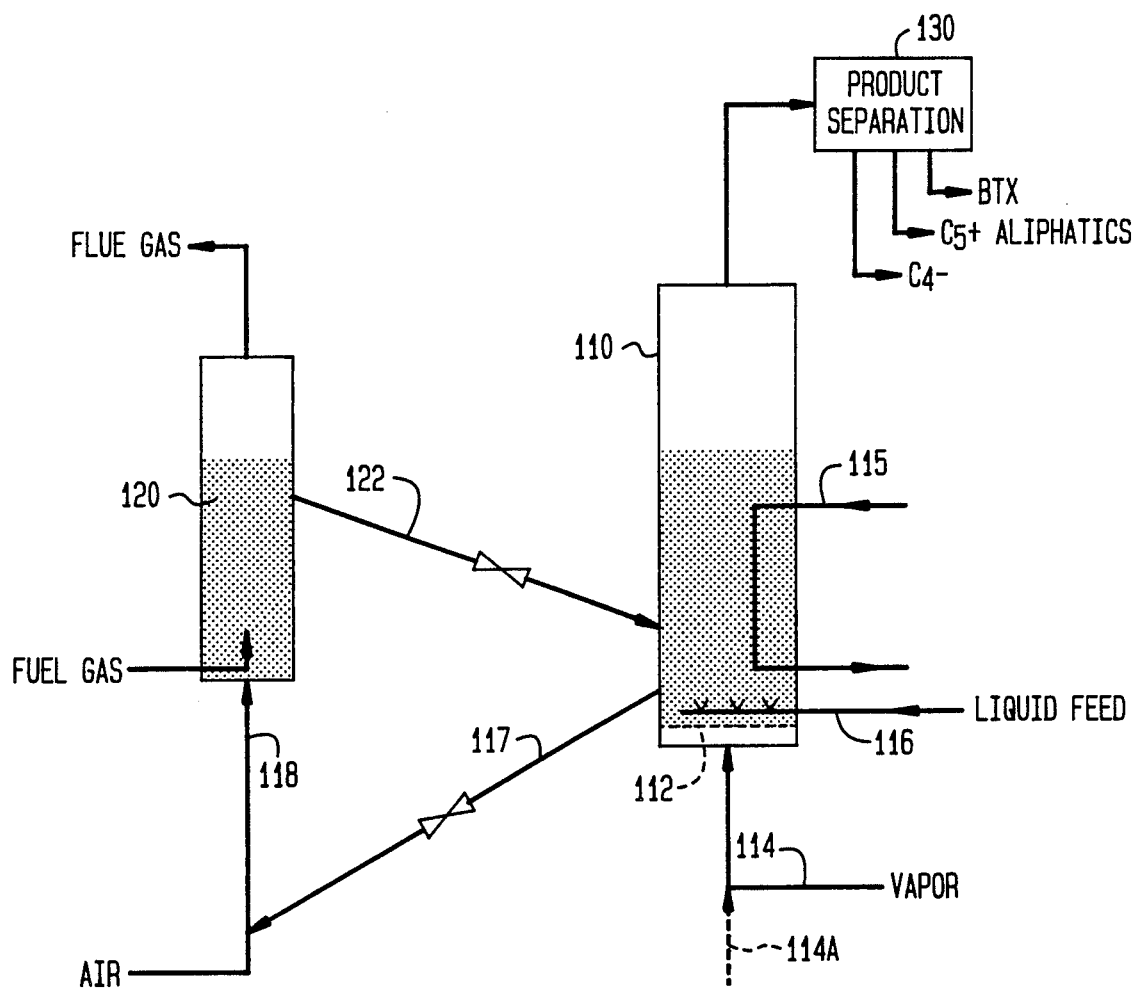

Referring now to FIG. 2, liquid methanol-containing raffinate 16 from the extractor is passed under pressure via feed conduit 116 for injection into vertical reactor vessel 110 above a feed distributor grid 112, which provides for distribution of hot vapor from etherification separation overhead passing via conduit 114 through the small diameter holes in the grid 112. Fluidization is effected in the bottom portion of the bed by upwardly flowing gas introduced via conduit 114, which may be supplemented with additional reactive gas 114A, such as FCC ethylenic fuel gas or the like. Although depicted without baffles, the vertical reaction zone can contain open end tubes above the grid for maintaining hydraulic constraints, as disclosed in U.S. Pat. No. 4,251,484 (Daviduk and Haddad). Optionally, a variety of horizontal baffles may be added to limit axial mixing in the reactor. Thermodynamic conditions in the reaction vessel can be controlled by adjusting liquid injection rate, vapor feed temperature, catalyst temperature and rate, or by heat exchange means 115.

Provision is made for withdrawing catalyst from above grid 112 by conduit means 117 provided with flow control valve means to control passage via air lift line 118 to the catalyst regeneration system in vessel 120 where coked catalyst particles are oxidatively regenerated in contact with air or other regeneration gas at high temperature. In order to add sufficient heat to the catalytic reaction zone 110, energy may be added by combustion of flue gas or other fuel stream in the regenerator. Regenerated catalyst is returned to the reactor fluid bed 110 through conduit means 122 provided with flow control valve means. The hot regenerated catalyst is charged to the catalyst bed sufficiently below the upper interface to achieve good mixing in the fluid bed. The rate of flow for regenerated catalyst may be adjusted to provide the degree of thermal input required for effecting endothermic conversion, and the rate will depend upon the amount and composition of the alkane components.

Initial fluidization is achieved by forcing a lift gas upwardly through the catalyst. A light gas, with or without diluent or recycle, may be charged at a bottom portion of the reactor beneath grid 112. Pressurized liquid feedstock is introduced above reactant distributor grid 112, and pumped to one or more spray nozzles. The liquid is dispersed into the bed of catalyst thereabove at a velocity sufficient to form a generally upwardly flowing suspension of atomized liquid reactant with the catalyst particles and lift gas. Advantageously, the liquid methanol-containing reactant feed is injected into the catalyst bed by atomizing the pressurized liquid feedstream to form readily dispersible liquid particles having an average size of 300 microns or less. This contributes to rapid vaporization of the liquid at process pressure. Exothermic conversion provides sufficient heat to vaporize the liquid quickly.

Cyclone catalyst particle separator means may be positioned in an upper portion of the reactor vessel. The product effluent separated from catalyst particles in the cyclone separating system then passes to effluent separation system 130. The product effluent is cooled and separated to recover $C_5+$ liquid gasoline range hydrocarbons or offgas, along with any byproduct water or catalyst fines carried over. A portion of the light gas effluent fraction may be recycled by compressing to form a motive gas for the liquid feed or recycle for use as lift gas. The recovered hydrocarbon product comprising $C_5+$ olefins and/or aromatics, paraffins and naphthenes is thereafter processed to obtain the desired aromatic and/or aliphatic products.

Optimized process conditions the turbulent bed has a superficial vapor velocity of about 0.2 to 2 meters per second (m/sec). At higher velocities entrainment of fine particles may become excessive and beyond 10 m/sec the entire bed may be transported out of the reaction zone. At lower velocities, the formation of large bubbles or gas voids can be detrimental to conversion. Even fine particles cannot be maintained effectively in a turbulent bed below about 0.1 m/sec.

A convenient measure of turbulent fluidization is the bed density. A typical turbulent bed has an operating density of about 100 to 500 $kg/m^3$, preferrably about 300 to 500, measured at the bottom of the reaction zone, becoming less dense toward the top of the reaction zone due to pressure drop and particle size differentiation. This density is generally between the catalyst concentration employed in dense beds and the dispersed transport systems. Pressure differential between two vertically spaced points in the reactor column can be measured to obtain the average bed density at such portion of the reaction zone. For instance, in a fluidized bed system employing ZSM-5 particles having a clean apparent density of 1.06 gm/cc and packed density of 0.85, an average fluidized bed density of about 300 to 500 $kg/m^3$ is satisfactory.

By virtue of the turbulence experienced in the turbulent regime, gas-solid contact in the catalytic reactor is improved, providing substantially complete conversion, enhanced selectivity and temperature uniformity. One main advantage of this technique is the inherent control of bubble size and characteristic bubble lifetime. Bubbles of the gaseous reaction mixture are small, random and short-lived, thus resulting in good contact between the gaseous reactants and the solid catalyst particles.

A significant advantage of the present invention is that operation in the turbulent fluidization regime is optimized to produce high octane $C_5+$ liquid in good yield. The weight hourly space velocity and uniform contact provides a close control of contact time between vapor and solid phases, typically about 3 to 25 seconds. Another advantage of operating in such a mode is the control of bubble size and life span, thus avoiding large scale gas by-passing in the reactor. The process of the present invention does not rely on internal baffles in the reactor for the purpose of bubble size control such as the baffles which are employed in the prior art dense bed processes discussed above.

As the superficial gas velocity is increased in the dense bed, eventually slugging conditions occur and with a further increase in the superficial gas velocity the slug flow breaks down into a turbulent regime. The transition velocity at which this turbulent regime occurs appears to decrease with particle size. The turbulent regime extends from the transition velocity to the so-called transport velocity, as described by Avidan et al in U.S. Pat. No. 4,547,616 and by Tabak et al. in U.S. Pat. No. 4,579,999, incorporated herein by reference.

A typical single pass reactor unit employs a temperature controlled catalyst zone with indirect heat exchange and/or adjustable gas quench, whereby heat can be removed or added, depending on the exothermicity or endothermicity of the reaction which in turn depends on the relative concentrations of olefin and paraffins in the feed. The reaction temperature can be carefully controlled in the usual operating range of about 250° C. to 650° C., preferably at average reactor temperature of 350° C. to 580° C. Energy conservation in the system may utilize at least a portion of the reactor exotherm heat value by exchanging hot reactor effluent with feedstock and/or recycle streams. Optional heat exchangers may recover heat from the effluent stream prior to fractionation. For highly endothermic reactions (high alkane concentration in the feed) additional heat can be supplied to the reactor from the regenerator. Various fuels can be burned in the regenerator to raise the temperature of the catalyst. It is preferred to operate the olefin conversion reactors at moderate pressure of about 100 to 3000 kPa (atmospheric to about 400 psig). The weight hourly space velocity (WHSV, based on total olefins in the fresh feedstock) usually is about 0.1–5 WHSV.

The present invention is particularly advantageous in the economic dewatering of crude methanol, thus avoiding expensive and energy-intensive prefractionation by distillation. By extracting methanol from the crude feedstock with olefinic hydrocarbon reactant liquid, substantial utilities and equipment savings are realized. Various modifications can be made to the system, especially in the choice of equipment and non-critical processing steps.

While the invention has been described by specific examples, there is no intent to limit the inventive concept as set forth in the following claims:

1. A continuous feedstock separation and etherification reactor system for converting crude methanol feedstock to methyl t-alkyl ether comprising:
   extractor means for introducing a crude feedstock liquid stream containing a minor about of water and a liquid olefinic hydrocarbon extraction stream under extraction conditions favorable to selective extraction o methanol, thereby providing an extract liquid phase rich in methanol and an aqueous liquid raffinate phase lean in methanol;
   conduit means for recovering said extract liquid phase and said raffinate phase from said extractor means as separate streams;
   first catalytic reactor means operatively connected for contacting the extract phase in a catalytic reaction zone with acid etherification catalyst in an etherification reaction zone under process conditions to convert a major portion of methanol to ether;
   effluent separation means for recovering ether product from unconverted olefinic hydrocarbon and methanol; and
   second catalytic reactor means operatively connected for contacting said raffinate phase with conversion catalyst in the presence of said unconverted olefinic hydrocarbon and methanol to produce normally liquid hydrocarbon product.

2. An improved reactor system for reacting crude aqueous methanol feedstock with iso-olefinic hydrocarbons to product $C_5+$ methyl t-alkyl ethers, which comprises:
   extractor means for introducing the aqueous methanol feedstock stream and a liquid hydrocarbon extraction solvent stream rich $C_4+$ isoalkene under liquid extraction conditions, including conduit means for recovering an organic extract phase comprising the hydrocarbon extractant and methanol and conduit means for recovering an aqueous methanol raffinate phase containing the major amount of water introduced with the feedstock and a minor amount of feedstock methanol;
   primary reactor means for reacting methanol and $C_4+$ isoalkene from the organic extract phase in contact with etherification catalyst under catalytic reaction conditions to produce ether product;
   etherification effluent fractionator means for separating ether product from unreacted methanol and $C_4+$ isoalkene; and
   secondary reactor means for converting methanol from the aqueous methanol raffinate phase concurrently with unreacted methanol and $C_4+$ isoalkene from etherificaton effluent fractionation to produce hydrocarbons.

3. The reactor system of claim 2 wherein etherification catalyst consists essentially of sulfonic acid resin.

4. A continuous reactor system for converting crude lower alkyl alcohol to lower alkyl t-alkyl ethers comprising the steps of:
   (a) an extraction unit including conduit means for introducing crude aqueous alcohol liquid feedstock for contact with a liquid hydrocarbon extraction solvent rich in $C_4+$ iso-alkene hydrocarbon under extraction conditions favorable to selective extraction of the alcohol, including conduit means for withdrawing an extract liquid stream rich in alcohol and an aqueous raffinate stream lean in alcohol;
   (b) primary etherification reactor means operatively connected to receive the extract liquid stream for charging liquid hydrocarbon extractant and extracted methanol substantially free of water to a first catalytic reaction zone containing acid etherification catalyst for converting alcohol and iso-alkene hydrocarbon to predominantly lower alkyl t-alkyl ether;
   (c) fractionation means for separating etherification effluent from reactor (b) to recover unreacted alcohol and light olefinic hydrocarbon overhead vapor and to recover liquid product containing ether product;

(d) secondary catalytic reactor means for upgrading olefinic overhead vapor from fractionator (c) to provide liquid hydrocarbon product; and (e) means for charging at least a portion of said aqueous raffinate stream from extraction means (a) for conversion of alcohol to hydrocarbons concurrently with olefin upgrading in reactor (d).

5. The reactor system of claim 4 wherein the acid etherification catalyst comprises ion exchange resin.

6. The reactor system of claim 4 the secondary reactor means contains acid medium pore zeolite catalyst.

* * * * *

UNITED STATES PATENT AND TRADEMARK OFFICE
CERTIFICATE OF CORRECTION

PATENT NO. : 5,064,623

DATED : November 12, 1991

INVENTOR(S) : Harandi et al.

It is certified that error appears in the above-identified patent and that said Letters Patent is hereby corrected as shown below:

Title page, item (54) and column 1, insert --OF-- before "RAFFINATE".

In the Abstract, line 7, insert --are-- before "recovered"
Column 9, line 60, "about" should read --amount--
Column 9, line 63, "o" should read --of--
Column 10, line 22, insert --in-- after "rich"

Signed and Sealed this

Thirteenth Day of April, 1993

Attest:

STEPHEN G. KUNIN

*Attesting Officer*        *Acting Commissioner of Patents and Trademarks*